United States Patent [19]

Durette

[11] Patent Number: 4,491,659
[45] Date of Patent: Jan. 1, 1985

[54] 2,6-DIDIOXY-3-AMINE,4-CARBOXY METHYLGLYCOSIDE AND RELATED COMPOUNDS

[75] Inventor: Philippe L. Durette, New Providence, N.J.

[73] Assignee: Merck & Co., Inc., Rahway, N.J.

[21] Appl. No.: 498,447

[22] Filed: May 26, 1983

Related U.S. Application Data

[63] Continuation of Ser. No. 248,174, Mar. 30, 1981, abandoned.

[51] Int. Cl.³ .................. C07H 15/04; C07H 5/06
[52] U.S. Cl. .................. 536/17.2; 536/4.1; 536/18.2; 536/18.7; 536/55; 549/291
[58] Field of Search ........... 549/291; 536/4.1, 17.2, 536/18.2, 18.7, 55

[56] References Cited

U.S. PATENT DOCUMENTS

3,480,613 11/1969 Walton .................. 536/4.1
3,496,196 2/1970 Suami et al. ............. 536/4.1

OTHER PUBLICATIONS

Kametani et al., "Jour. of the American Chemical Society", vol. 102, No. 6, Mar. 12, 1982, pp. 2060–2064.

*Primary Examiner*—Johnnie R. Brown
*Attorney, Agent, or Firm*—Thomas E. Arther; Hesna J. Pfeiffer

[57] ABSTRACT

Disclosed is a chiral, total synthesis of thienamycin from D-glucose which proceeds via intermediates I, II, III and IV to known lactone V which is known to be useful via acid VI in the total synthesis of thienamycin (VII):

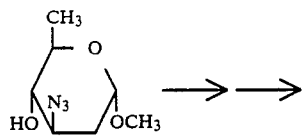

I

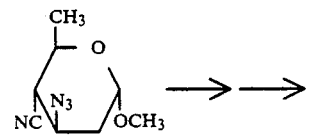

II

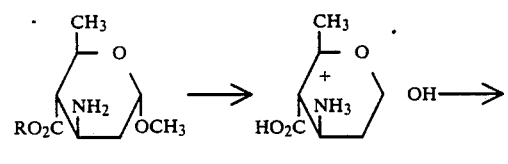

III          IV

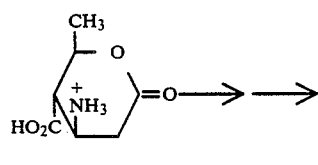

V

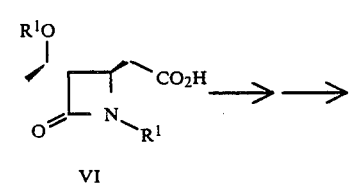

VI

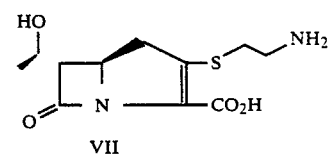

VII wherein $R^1$ is hydrogen or a removable protecting group; R is a removable protecting group.

2 Claims, No Drawings

2,6-DIDIOXY-3-AMINE,4-CARBOXY METHYLGLYCOSIDE AND RELATED COMPOUNDS

BACKGROUND OF THE INVENTION

This is a continuation of application Ser. No. 248,174 filed Mar. 30, 1981, now abandoned.

This invention relates to the chiral total synthesis of thienamycin from D-glucose (dextrose).

In its broadest terms, the process proceeds from glucose via intermediates I, II, III and IV and encounters lactone V which is known to be useful via acid VI to be useful in the total synthesis of thienamycin (VII).

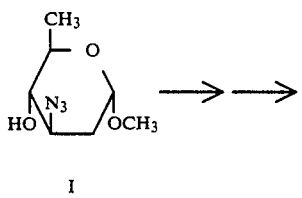

I

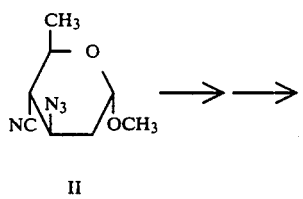

II

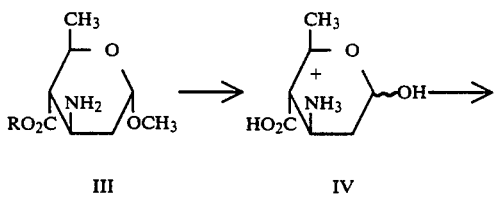

III            IV

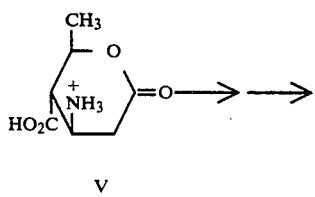

V

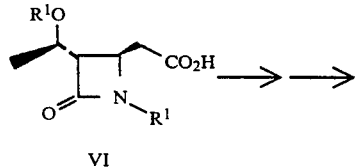

VI

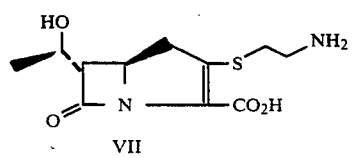

VII wherein $R^1$ is hydrogen or a removable protecting group, such as a triorganosilyl group; and R is a removable protecting group, such as lower alkyl having 1–6 carbon atoms or aralkyl having 7–10 carbon atoms, for example, methyl, ethyl, propyl, benzyl, and the like. Relative to $R^1$, suitable organo moieties under the classification "triorganosilyl" include and are independently selected from: alkyl having 1–6 carbon atoms, phenyl and phenylalkly having 7–10 carbon atoms.

The following concurrently filed, commonly assigned U.S. patent applications are incorporated herein by reference: Ser. No. 248,175, now U.S. Pat. No. 4,415,731; Ser. No. 248,178, now U.S. Pat. No. 4,348,325; Ser. No. 248,177, now U.S. Pat. No. 4,384,998; and Ser. No. 248,176, now U.S. Pat. No. 4,324,900; all filed Mar. 30, 1981 [Merck & Co., Inc., all of Philippe L. Durette]. Also incorporated by reference are U.S. patent application Ser. No. 112,058 filed Jan. 14, 1980, now abandoned; U.S. Pat. No. 4,234,596 issued Nov. 18, 1980 and EPO Patent Application No. 79202307.1 filed May 1, 1979, publication No. 007973, which publications and pending application disclose schemes of total synthesis which can be fed by common intermediates made available by the presently disclosed and claimed process.

DETAILED DESCRIPTION OF THE INVENTION

The process of the present invention may conveniently be represented by the following reaction diagram:

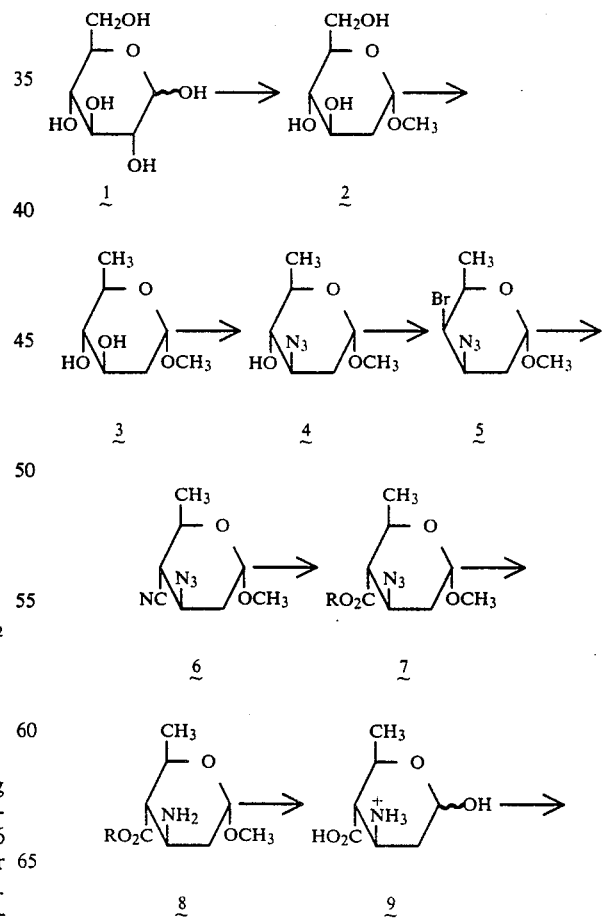

-continued

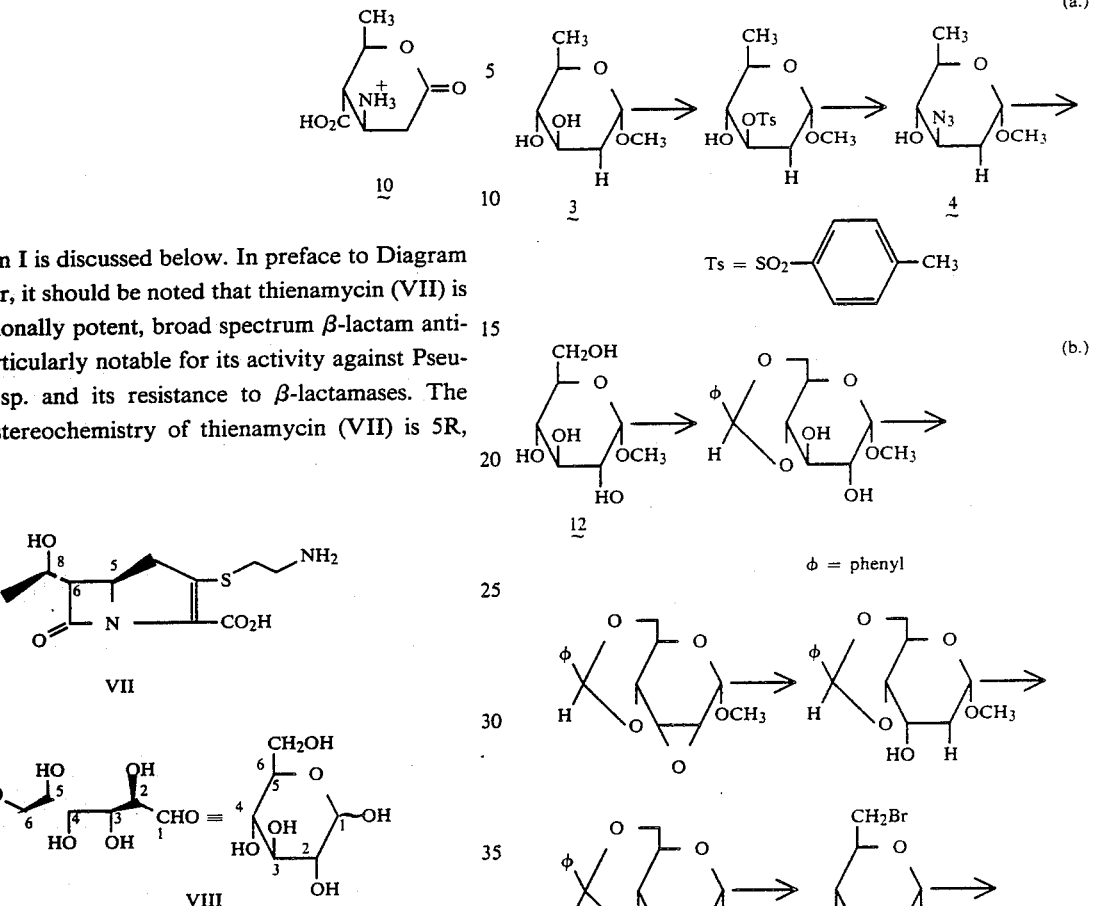

Diagram I is discussed below. In preface to Diagram I, however, it should be noted that thienamycin (VII) is an exceptionally potent, broad spectrum β-lactam antibiotic, particularly notable for its activity against Pseudomonas sp. and its resistance to β-lactamases. The absolute stereochemistry of thienamycin (VII) is 5R, 6S, 8R.

The present invention comprises a chiral total synthesis of thienamycin starting from the readily available sugar, D-glucose (dextrose) (VIII). The 5R, 6S, 8R stereochemistry of thienamycin is inherent in the D-glucose structural symmetry, as depicted in VIII (chiral centers 3, 4, and 5). D-glucose is functionalized to afford optically active lactone V, via intermediates I, II, III, and IV, previously shown. Compound V is known to be useful via azetidinone acid VI in the total synthesis of thienamycin (VII).

A key intermediate in the conversion of D-glucose into lactone V is methyl 3-azido-2,3,6-trideoxy-αD-arabino-hexopyranoside (I). Compound I is transformed into methyl 3-azido-4-C-cyano-2,3, 4-6-tetradeoxy-α-D-arabino-hexopyranoside (II), which is then converted, as depicted in the diagram above and in words relative to that diagram, into amino ester III, then to amino acid IV, and finally to amino acid lactone V.

Methyl 3-azido-2,3,6-trideoxy-α-D-arabino-hexopyranoside (4) is obtained either from methyl 2,6-dideoxy-α-D-arabino-hexopyranoside (3) or from methyl-α-D-glucopyranoside (12), as represented by the following reaction diagrams, respectively:

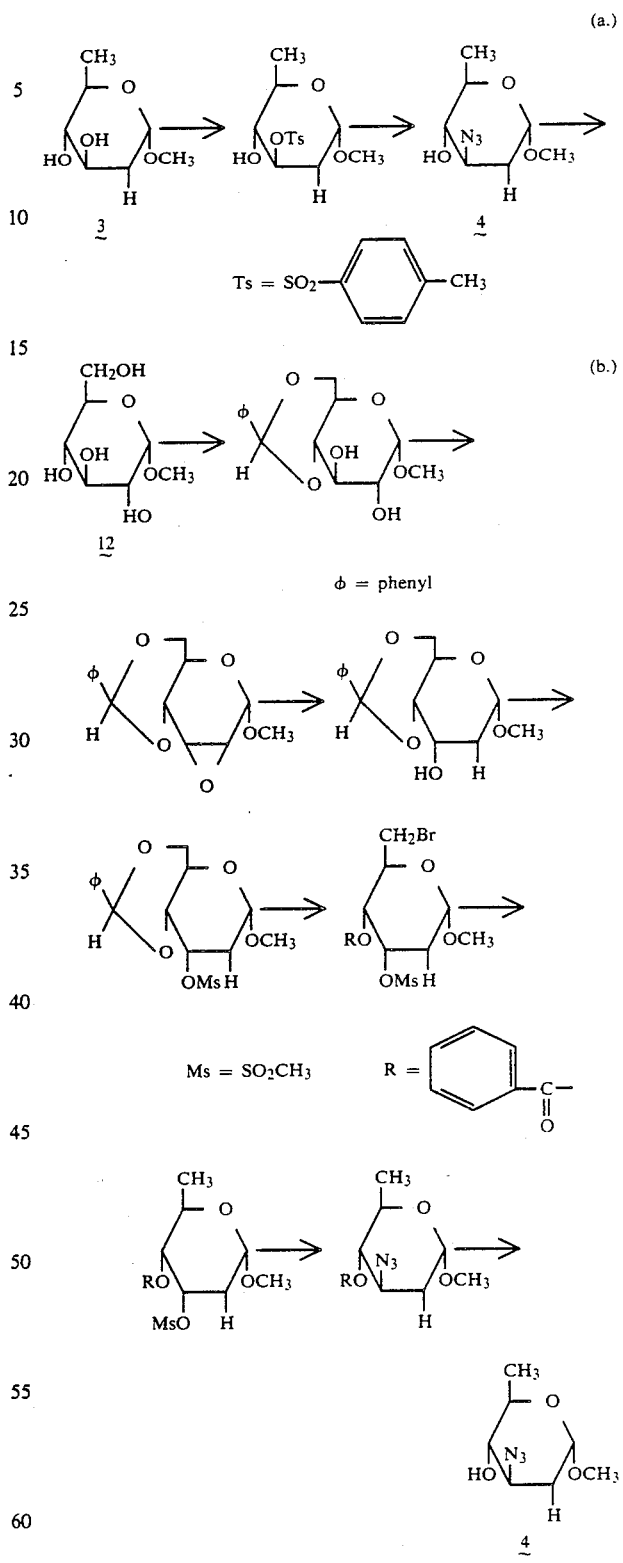

Methyl 2,6-dideoxy-α-D-arabino-hexopyranoside (3) is obtained from D-glucose (1), via 2-deoxy-D-glucose (13), or D-glucal (14), and methyl 2-deoxy-α-D-glucopyranoside (2), as represented by the following reaction diagram:

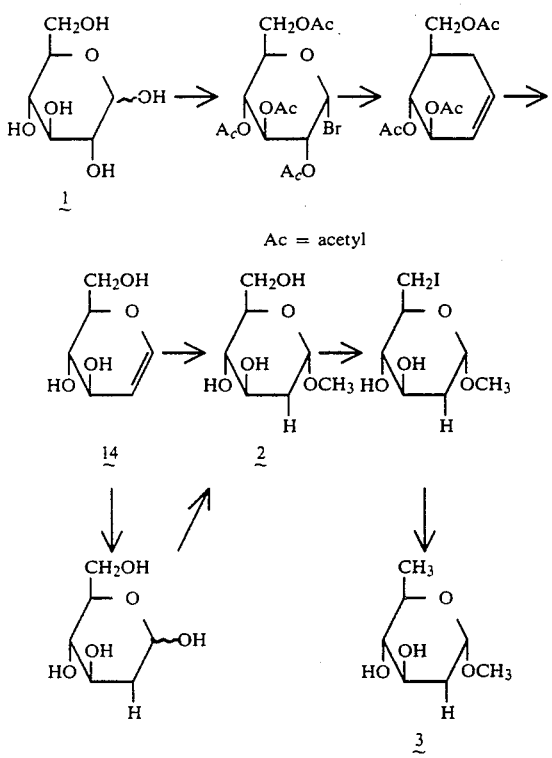

Ac = acetyl

Methyl α-D-glucopyranoside (12) is obtained from D-glucose (1) as shown below,

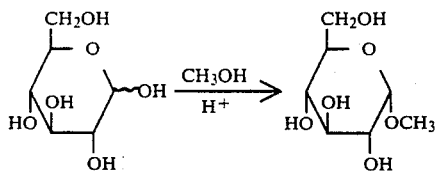

Now, returning to Diagram I, above, the transformation 1→2 is known. Typically D-glucose (1) is converted into methyl 2-deoxy-α-D-glucopyranoside (2) by the following sequence of reactions: (a) acetic anhydride and pyridine or acetic anhydride and sodium acetate to give penta-O-acetyl-D-glucopyranose; (b) hydrogen bromide in acetic acid to afford tetra-O-acetyl-α-D-glucopyranosyl bromide; (c) zinc and acetic acid to yield tri-O-acetyl-D-glucal; (d) sodium (or sodium methoxide) in methanol to give D-glucal; and (e) methanolic hydrogen chloride to yield 2. Conversion of D-glucal (or 2-deoxy-D-glucose) into 2 is reported in I. W. Hughes, et. al., *J. Chem. Soc.*, 2846 (1949).

The transformation 2→3 is accomplished by treating 2 in a solvent such as toluene, benzene, dimethylformamide, dichloromethane, or the like with an iodinating agent (or other halogenating agent), such as methyltriphenoxyphosphonium iodide, iodotriphenoxyphosphonium iodide, triphenyphosphine-N-iodosuccinimide; triphenylphosphinetetraiodomethane; triphenylphosphine-2,4,5-triiodoimidazole; triphenylphosphine, iodine, and imidazole; or the like at a temperature of from 20° to 100° C. for from 1 to 24 hours.

The hydrogenolysis to yield compound 3 is typically conducted in a solvent, such as methanol, ethanol, ethyl acetate, or the like, at a temperature of from 20° to 50° C. in the presence of a catalyst such as Raney nickel, palladium-on-charcoal, palladium black, palladium hydroxide, or the like, under a hydrogen pressure of from 1 to 5 atmospheres.

Transformation 3→4 is accomplished in a solvent such as pyridine or dichloromethane, chloroform, or the like with p-toluenesulfonyl chloride, p-toluenesulfonic anhydride, or the like in the presence of a base such as Et$_3$N, iPr$_2$NEt, pyridine, 4-dimethylaminopyridine, or the like, at a temperature of from −15° C. to +10° C. for from 24 hours to 10 days to yield the C-3 tosylate, which upon treatment, in a solvent such as ethanol, methanol, or the like, with alcoholic base, such as ethanolic sodium hydroxide, ethanolic potassium hydroxide, methanolic sodium hydroxide, methanolic potassium hydroxide, or the like, followed by treatment with an alkali azide, such as lithium azide, sodium azide, potassium azide, or the like in the presence of ammonium chloride at a temperature of from 50° C. to 100° C. from 1 hour to 24 hours yields the azide 4.

Treatment of 4 in a solvent such as dichloromethane, chloroform, or the like with trifluoromethanesulfonyl chloride, trifluoromethanesulfonic anhydride, or the like in the presence of a base such as Et$_3$N, iPr$_2$NEt, pyridine, 4-dimethylaminopyridine or the like at a temperature of from −76° C. to 0° C. for from 20 minutes to 2 hours, followed by treatment with a brominating agent, such as lithium bromide, sodium bromide, tetraethylammonium bromide, tetra-n-butylammonium bromide or the like in a solvent such as, dichloromethane, acetonitrile tetrahydrofuran, dimethylformamide, or the like at a temperature of from 20° C. to 100° C. for from 30 minutes to 5 hours, yields the 4-bromo-4-deoxy sugar 5 which upon treatment with sodium cyanide, potassium cyanide (in the presence or absence of a crown ether), tetraethylammonium cyanide, tetra-n-butylammonium cyanide, tetraethylammonium chloride-sodium cyanide, or the like in a solvent such as dichloromethane, acetonitrile, tetrahydrofuran, dimethylformamide, dimethylsulfoxide, hexamethylphosphoramide, or the like at a temperature of from 30° C. to 150° C. for from 15 minutes to 24 hours yields compound 6.

Alcoholysis 6→7 is accomplished by treating 6 either (a) in an alcohol such as methanol, ethanol, propanol, or the like with an alkali alkoxide, such as sodium methoxide, sodium ethoxide, sodium propoxide, or the like, at a temperature of from 0° to 30° C. for from 1 to 24 hours followed by neutralization with a cation-exchange resin in the H$^+$ cycle, such as Amberlite IR-120, Bio-Rad AG50W, Dowex 50W, or the like; or (b) in a solvent such as diethyl ether, dichloromethane, chloroform, or the like with an alcohol, such as methanol, ethanol, propanol, or the like saturated at 0° C. with dry hydrogen chloride gas, at a temperature of from 0° to 30° C. for from 2 to 24 hours, followed by hydrolysis at 0° C. The value of R is determined by the identity of the alcohol taken in reaction.

Conversion of azido ester 7 into amino ester 8 is accomplished by treating 7 in a solvent, such as methanol, ethanol, ethyl acetate, acetic acid, or the like at a temperature of from 20° to 50° C. in the presence of a catalyst such as palladium-on-charcoal, palladium black, palladium hydroxide, Raney nickel, platinum oxide, nickel boride, or the like under a hydrogen pressure of from 1 to 5 atmospheres.

Transformation 8→9 is accomplished by mild aqueous hydrolysis in the presence of an acid, such as hydrochloric, sulfuric, or the like. Typically, the hydrolysis is conducted at a temperature of from 20° to 110° C. for from 20 minutes to 10 hours.

Formation of lactone 10 is accomplished by treatment of hemiacetal 9 with an oxidant, such as bromine water; Pt-O₂; silver carbonate on Celite (Fetizon reagent); Jones reagent; pyridinium dichromate; pyridinium chlorochromate; dimethylsulfoxide-acetic anhydride; silver picolinate in water, DMSO, or DMSO-diglyme; or the like.

In the foregoing word description of the above schematic reaction diagram for the total synthesis of thienamycin, it is to be understood that there is considerable latitude in selection of precise reaction parameters. Suggestion of this latitude and its breadth is generally indicated by the enumeration of equivalent solvent systems, temperature ranges, protecting groups, and range of identities of involved reagents. Further, it is to be understood that the presentation of the synthetic scheme as comprising distinct steps in a given sequence is more in the nature of a descriptive convenience than as a necessary requirement; for one will recognize that the mechanically dissected scheme represents a unified scheme of synthesis and that certain steps, in actual practice, are capable of being merged, conducted simultaneously, or effected in a reverse sequence without materially altering the progress of synthesis.

The following examples recite a precise scheme of total synthesis. It is to be understood that the purpose of this recitation is to further illustrate the total synthesis and not to impose any limitation.

EXAMPLE 1

Step A

Methyl 3-azido-4-C-carbomethoxy-2,3,4,6-tetradeoxy-α-D-arabino-hexopyranoside

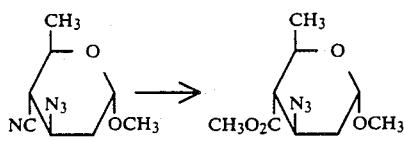

Dry hydrogen chloride gas is bubbled for 1 hour through a solution of methyl 3-azido-4-C-cyano-2, 3, 4, 6-tetradeoxy-α-D-arabino-hexopyranoside (1.41 g, 7.19 mmol) in diethyl ether (8 ml) and absolute methanol (8 ml) cooled in an ice-bath. The solution is then allowed to stand overnight at room temperature and evaporated under vacuum. The residue is taken up in dichloromethane, washed with saturated sodium hydrogencarbonate solution, and evaporated. The residue is chromatographed on a column of silica gel (Merck No. 7734) (5:1 diethyl ether-hexane) to afford 1.23 g (75%) of the desired azido ester; IR (CHCl₃):1733 (C=O), 2095 (N₃); ¹HNMR (300 MHz, CDCl₃): δ1.18 (d, C-CH₃), 1.64 (td, H-2 ax), 2.08 (t, H-3), 2.16 (m, H-2 eq), 3.36 (s, OCH₃), 3.76 (s, CO₂CH₃), 3.88–4.08 (m, H-3,5), 4.84 ppm (broad d, H-1).

Step B

Methyl 3-amino-4-C-carbomethoxy-2,3,4,6-tetradeoxy-α-D-arabino-hexopyranoside

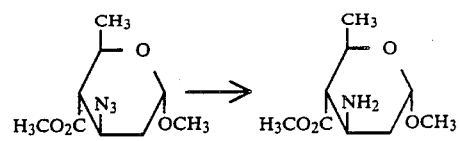

A mixture of methyl 3-azido-4-C-carbomethoxy-2,3,4,6-tetradeoxy-α-D-arabino-hexopyranoside (1.19 g, 5.19 mmol) and 5% palladium-on-charcoal (500 mg) in methanol (35 ml) is hydrogenated at a pressure of 1 atmosphere for 5 hours at room temperature. The catalyst is then removed by filtration through Celite and the filtrate evaporated and dried in vacuo to give TLC-chromatographically-homogeneous, ninhydrin positive amino ester; yield 1.01 g (96%).

Step C

3-Amino-4-C-carboxy-2,3,4,6-tetradeoxy-D-arabino-hexose hydrochloride

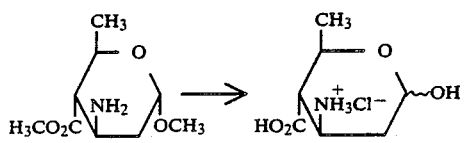

A mixture of methyl 3-amino-4-C-carbomethoxy-2,3,4,6-tetradeoxy-α-D-arabino-hexopyranoside (995 mg, 4.90 mmol) in concentrated hydrochloric acid (15 ml) is heated at reflux temperature for 3 hours. The cooled mixture is then evaporated under vacuum, and the residue is triturated with diethyl ether to afford the amino acid hydrochloride, yield 943 mg (91%).

Step D

3-Amino-4-C-carboxy-2,3,4,6-tetradeoxy-D-arabino-hexono-1,5-lactone hydrochloride (tetrahydro-2β-methyl-6-oxo-4β-amino-2H-pyran-3α-carboxylic acid hydrochloride)

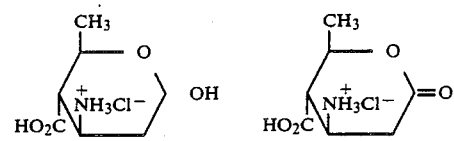

A solution of 3-amino-4-C-carboxy-2,3,4,6-tetradeoxy-D-arabino-hexose hydrochloride (935 mg, 4.42 mmol) in water (25 ml) is stirred with bromine (1.95 ml) for 48 h at room temperature. After elimination of excess bromine and evaporation of the solution, the residue is crystallized from acetic acid to afford pure lactone.

What is claimed is:
1. A process for preparing

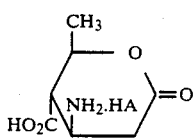

wherein: A is an anion derived from hydrochloric or sulfuric acid; comprising the steps of: hydrolyzing in the presence of aqueous acid:

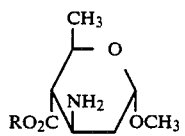

to form:

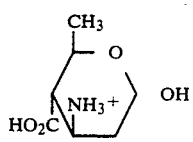

followed by treatment with an oxidant selected from bromine water, Pt-O₂, silver carbonate, Jones reagent, pyridinium dichromate, pyridinium chlorochromate, dimethylsulfoxide-acetic anhydride, silver picolinate in water, dimethylsulfoxide, or dimethylsulfoxidediglyme wherein R is selected from the group consisting of alkyl having 1-6 carbon atoms, phenylalkyl having 7-10 carbon atoms.

2. A compound selected from the group consisting of:

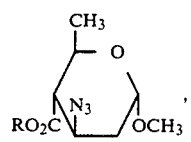

and

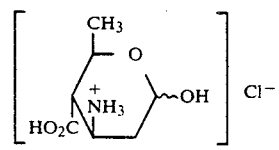

wherein: R is selected from the group consisting of alkyl having 1-6 carbon atoms and, phenylalkyl having 7-10 carbon atoms.

* * * * *